United States Patent [19]

Baumberg

[11] Patent Number: 4,489,731
[45] Date of Patent: Dec. 25, 1984

[54] PULSE RATE MONITOR

[75] Inventor: Iosif Baumberg, Brooklyn, N.Y.

[73] Assignee: H & B Technologies, Inc., New York, N.Y.

[21] Appl. No.: 463,815

[22] Filed: Feb. 4, 1983

[51] Int. Cl.$^3$ .............................................. A61B 5/02
[52] U.S. Cl. .................................... 128/690; 128/687
[58] Field of Search .............................. 128/687–690, 128/672, 668

[56] References Cited

U.S. PATENT DOCUMENTS

| 3,661,147 | 5/1972 | Mason et al. | 128/689 |
| 3,717,140 | 2/1973 | Greenwood | 128/689 |
| 3,742,938 | 7/1973 | Stern | 128/687 |
| 3,908,640 | 9/1975 | Page | 128/689 |
| 4,009,708 | 3/1977 | Fay, Jr. | 128/690 |
| 4,058,118 | 11/1977 | Stupay et al. | 128/690 |
| 4,063,551 | 12/1977 | Sweeney | 128/690 X |
| 4,120,296 | 10/1978 | Prinz | 128/690 |
| 4,367,752 | 1/1983 | Jimenez et al. | 128/689 |
| 4,406,290 | 9/1983 | Walbeoffe-Wilson et al. | 128/690 X |

FOREIGN PATENT DOCUMENTS

| 2509660 | 9/1976 | Fed. Rep. of Germany | 128/689 |
| 2624732 | 12/1976 | Fed. Rep. of Germany | 128/690 |
| 2944402 | 5/1981 | Fed. Rep. of Germany | 128/689 |
| 2052752 | 1/1981 | United Kingdom | 128/690 |
| 659144 | 4/1979 | U.S.S.R. | 128/689 |
| 805996 | 2/1981 | U.S.S.R. | 128/687 |

OTHER PUBLICATIONS

Ludwig, "Heart or Respiration-Rate Calculator", *Med. and Biol. Eng. and Comput.*, 11-1977; vol. 15, No. 6, pp. 700-702.

Primary Examiner—Lee S. Cohen
Assistant Examiner—Angela D. Sykes
Attorney, Agent, or Firm—David M. Warren

[57] ABSTRACT

A heart monitor is constructed with a housing that is to be worn by a person, the housing including a display of heartbeat data and a detector of pulsations of the heart. The interpulse intervals between successive pulses, or heart beats, are measured to provide heart-beat data which includes the frequency of occurrence of various ranges of interpulse intervals, as well as an average value of interpulse intervals. The display positions the average value in registration with a corresponding range of the frequency of occurrence. The average value is measured by counting pulses through a succession of interpulse intervals. The frequency of occurrence is measured by a set of sequentially activated gating circuits with counters coupled thereto for counting the occurrences of interpulse intervals of differing durations.

18 Claims, 6 Drawing Figures

PULSE RATE MONITOR

BACKGROUND OF THE INVENTION

This invention relates to a heart monitoring device and, more particularly, to a device for the concurrent measurement and display of pulse rate and variations thereof.

Electronic equipment is employed today in hospitals and other health-care institutions for the monitoring of a person's heart activity. One important measurement parameter is the rate of occurrence of heart pulsations. In a healthy person, the pulse rate is substantially uniform throughout the duration of a person's activity, the rate varying with changes in the person's activity when the heart may be called upon to pump at a higher or lower rate. Thus, it is readily appreciated that devices for the measuring of pulse rate are most useful in the detection and treatment of disease. The measurement process may necessitate complex electronic equipment, the complexity of the measurement process depending upon the pattern of the heart pulsations.

The monitoring of a person's pulse rate can be a complex process due to variations in the pulse rate. In a person suffering from a heart ailment, for example, a heart ailment characterized by an irregular beat known as arrhythmia, a problem arises in that a single numerical value of pulse rate does not adequately describe the heartbeat pattern. A set of numerical values is most useful for describing the percentage of beats that occur at each of various pulse rates that may be observed. The numerical values can be expressed as a frequency of occurrence of heart beats, or as an interval of time between successive heart beats. In addition, the heart beat should be monitored during a person's regular activity so that information can be gathered over an extended period of time. Such extended observation, which could be accomplished if it were possible for a patient to wear a monitoring device, would provide a more complete and useful description of the patient's condition.

A further problem is found in the electronic equipment used to monitor the heart beats. The equipment employed in hospitals has the usual form of laboratory test equipment which is clearly too big and too heavy to be worn and carried about by a patient. Additional electronic circuitry to provide data analysis would make equipment even more difficult to carry about. Thus, existing equipment militates against the continuous wearing of electronic equipment and, therefore, inhibits the gathering of data during a person's normal daily activity. As a result, the physician attending a patient is denied useful data which would allow for better health care.

SUMMARY OF THE INVENTION

The foregoing problems are overcome and other advantages are provided by a heart-beat monitoring device which measures the elapsed time between heart beats and presents a statistical analysis of data of the heart beat. The device is sufficiently small to be worn on a person's wrist, which location is also convenient for sensing the person's pulse and for reading a presentation of data of the heart beat. The measurement of the elapsed time is accomplished with the aid of a detector of a person's pulse, a pulsation being detected at the person's wrist for each beat of the heart. The data is based on the elapsed times between pulses, or interpulse intervals, and is presented as a histogram with percentages of occurrence of long and short intervals, along with the duration of an average interval. In the presentation, the data is arranged in a format in a display, analogous to a watch dial, wherein all the data can be assimilated rapidly in a glance at the display by the person wearing the device, or by his physician.

In the construction of the histogram, the measurements of the interpulse intervals are segregated, preferably, into several ranges of magnitude so as to separately present the percentage of intervals falling in the range of short intervals, long intervals and other ranges of intervals in between. With the simultaneous presentation of average magnitude of all the measured intervals, the display thereby provides a complete picture of the recent history of the pattern of heart activity to facilitate the treatment and diagnosis of heart disease.

The device is provided with two modes of measurement, one mode providing for the direct measurement of each interpulse interval, and the other mode employing a statistical sampling of interpulse intervals. The direct-measurement mode is useful for measuring times of relatively short duration, while the statistical-sampling mode is useful for measuring time of relatively long duration.

BRIEF DESCRIPTION OF THE DRAWINGS

The foregoing aspects and other features of the invention are explained in the following description taken in connection with the accompanying drawings wherein.

DETAILED DESCRIPTION

Figure 1:
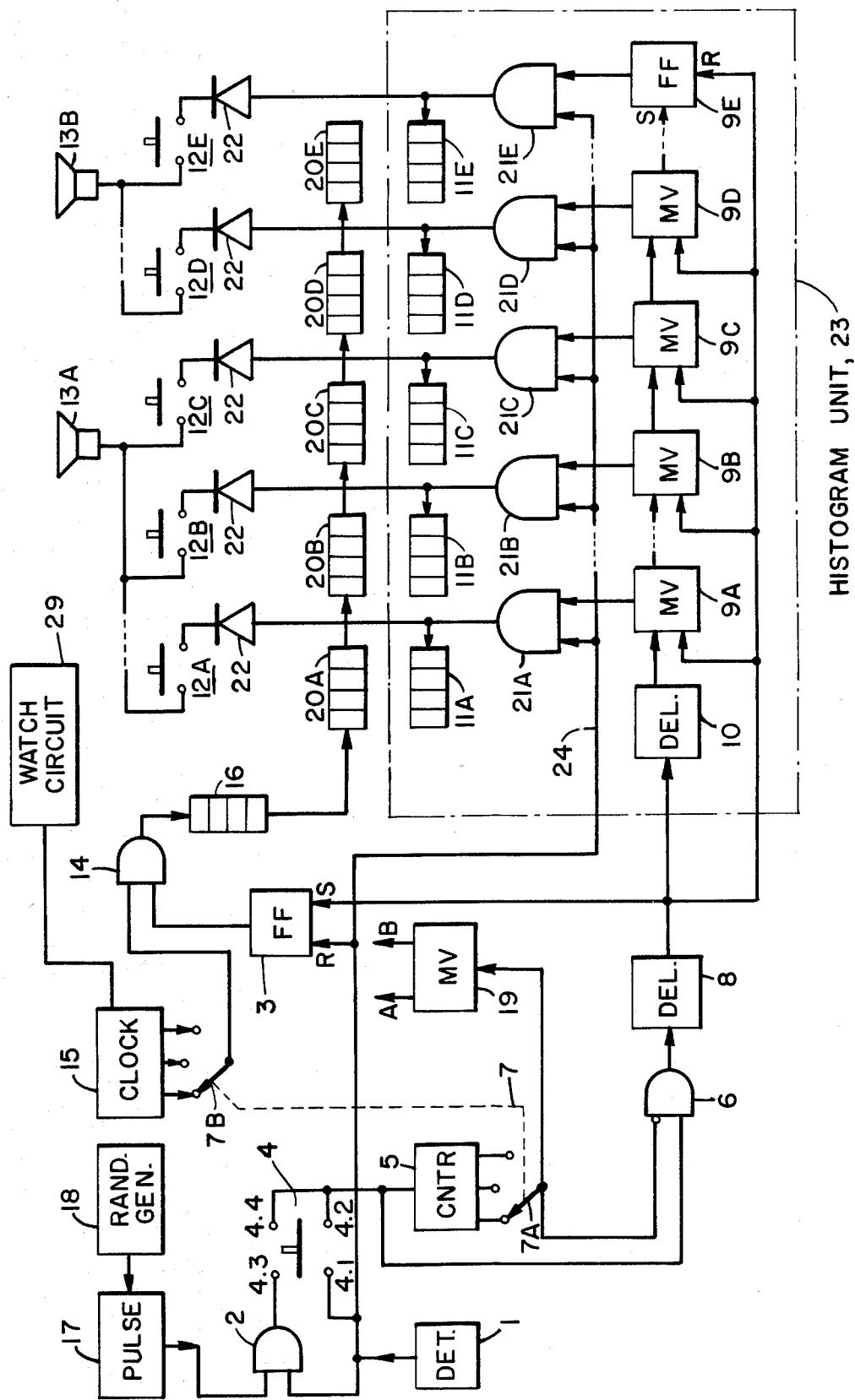
FIG. 1 is a schematic drawing of the electrical circuitry of the invention.
Figure 2:
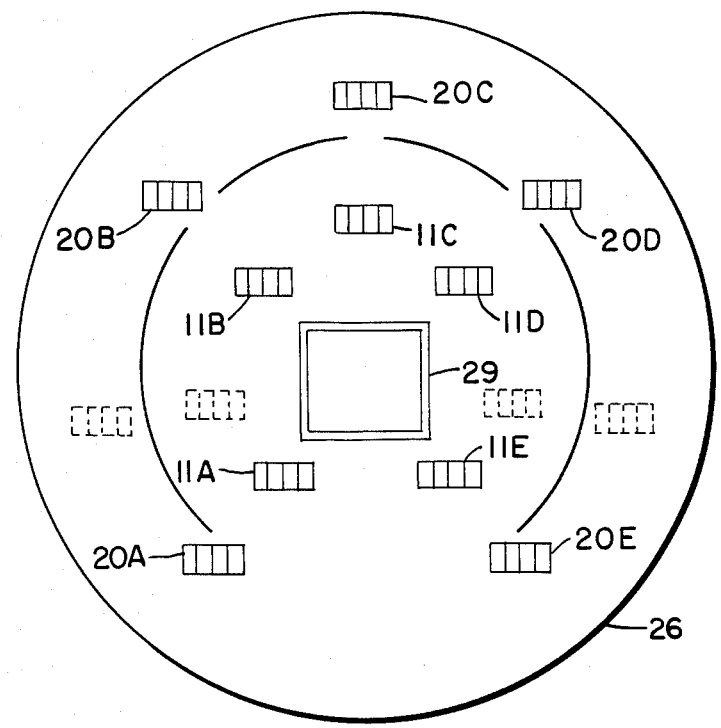
FIG. 2 is a plan view of the monitoring device of the invention, the figure showing the arrangement of indicators on a display of the monitoring device.
Figure 3:
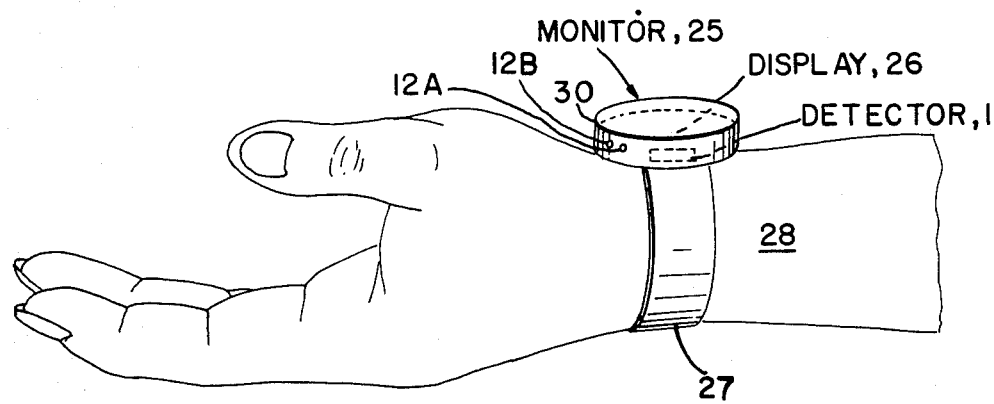
FIG. 3 shows a mode of wearing the monitoring device on a person's wrist with a detector of the device being positioned for detecting pulses of the heart beat.

The heart-beat monitoring device is constructed, in accordance with the invention, as portrayed in FIGS. 1, 2 and 3. FIG. 1 shows a schematic representation of the electrical system of the device, while FIGS. 2 and 3 show physical features and the mode of wearing the device on a person's wrist. The electrical circuitry, a source of power such as a battery (not shown) and a display of the heart-beat data are all enclosed within a case, in the general shape of a wristwatch, which is sufficiently small to be conveniently worn on a person's wrist. The electrical circuitry provides for the detection of the person's pulse so as to count the heart beats, the electrical circuitry also providing for an analysis of the intervals of time elapsed between successive heart beats for presentation of the heart-beat data in a manner which is readily observed by the person.

As shown in FIG. 1, the electronic circuitry comprises a detector 1, an AND gate 2, a flip-flop 3, a switch 4, a counter 5, an AND gate 6, and a switch 7 composed of two sections 7A and 7B which are ganged together. The detector 1 detects sonic vibrations and is of well-known construction. For example, the detector 1 may comprise a piezoelectric crystal or magnetic coil pickup (not shown) which is coupled by suitable amplifying and filtering circuitry, all of which are well-known and in current use, to provide an electrical signal at the output terminal of the detector 1 in the form of a pulse signal. The pulse signal results from the detection of a person's pulse resulting from the beating of his heart. The AND gates 2 and 6 each provide a logic 1, or a high, output signal upon the coincidence of the two input signals, the output signal being a logic 0, or low, signal in the event that one or both of the input signals are absent. In the case of the gate 2, the output logic 1 signal is attained when both input signals are of logic 1. In the case of the gate 6, the input terminal, which is coupled to the switch 7, is complemented so that an output, logic 1 signal is attained when the input signal from the switch 4 is a logic 1 while the input signal from the switch 7 is a logic 0.

The flip-flop 3 is of the set-reset form and provides a logic 1 signal at the output terminal in response to the setting of the flip-flop by a signal at the terminal S. The output signal of the flip-flop reverts to a logic 0 in response to a reset signal applied to terminal R. The switch 4 is manually operated to couple together either the terminal 4.1 to the terminal 4.2 or, alternatively, to couple together the terminal 4.3 to the terminal 4.4. When the terminals 4.1 and 4.2 are connected, electric signals pass from the detector 1 directly to the counter 5 and the gate 6 for the direct-measurement mode of operation as will be described subsequently. When the terminals 4.3 and 4.4 are connected, the signals of the detector pass via the gate 2 to the counter 5 and the gate 6 for a statistical-measurement mode of operation as will be described subsequently. In both modes of operation, the signals of the detector 1 are connected to the reset terminal of the flip-flop 3.

The counter 5 counts pulses from the detector 1, the counter counting 100 pulses and providing an output logic 1 signal at the output terminal shown on the left side of the counter 5. The counter continues to count up to 1,000 pulses and, on the 1001 pulse, provides an output logic 1 signal on the output terminal shown in the middle of the counter 5. The counter 5 continues to count still further to 10,000 pulses and, upon a count of 10,001, provides an output logic 1 signal at the output terminal to the right side of the counter 5. The switch 7 is manually operated to select, via switch section 7B, the desired one of the three output terminals of the counter 5.

The circuit further comprises a delay unit 8, multivibrators 9 of which individual ones thereof are further identified by the legends A–D, and a flip-flop 9E. The flip-flop 9E is of the set-reset type and has a set input terminal S and a reset terminal R. A further delay unit 10 is also included within the circuit. The output signal of the AND gate 6 is coupled by the delay unit 8 to the set terminal of the flip-flop 3, and also to the delay unit 10. The delay imparted to the signal of the gate 6 by the delay unit 8 is much smaller than the delay imparted by the delay unit 10. Both delays are smaller than the smallest interval of time anticipated between the successive occurrences of two heart beats. The output signal of the delay unit 10 triggers the multivibrator 9A, the multivibrator 9A providing a pulse of a predetermined duration at its output terminal, unless earlier reset by a following output signal from the delay unit 8. The multivibrators 9 are arranged in a serial format, the series including several or more of the multivibrators, of which only four of the multivibrators are shown, these multivibrators being designated 9A–9D. The output terminals of the respective multivibrators 9 are coupled to the input terminals of the following multivibrators 9 and, similarly, the output terminal of the last multivibrator 9D is coupled to the set input terminal of the flip-flop 9E. Thereby, upon the completion of the first output pulse of the multivibrator 9A, the trailing edge of that pulse triggers the multivibrator 9B to produce its output pulse. Similarly, upon the conclusion of the output pulse of the multivibrator 9B, the trailing edge triggers the multivibrator 9C to produce its output pulse, the sequence of operations proceeding through the remainder of the series of multivibrators. The trailing edge of the output pulse of the last multivibrator 9D sets the flip-flop 9E to provide a logic 1 signal at the output terminal of the flip-flop 9E. The sequence of operations wherein one multivibrator triggers the next multivibrator continues until the occurrence of a following signal from the delay unit 8 to reset all of the multivibrators 9 and the flip-flop 9E. When reset, the flip-flop 9E outputs a logic 0 signal.

Figure 4:
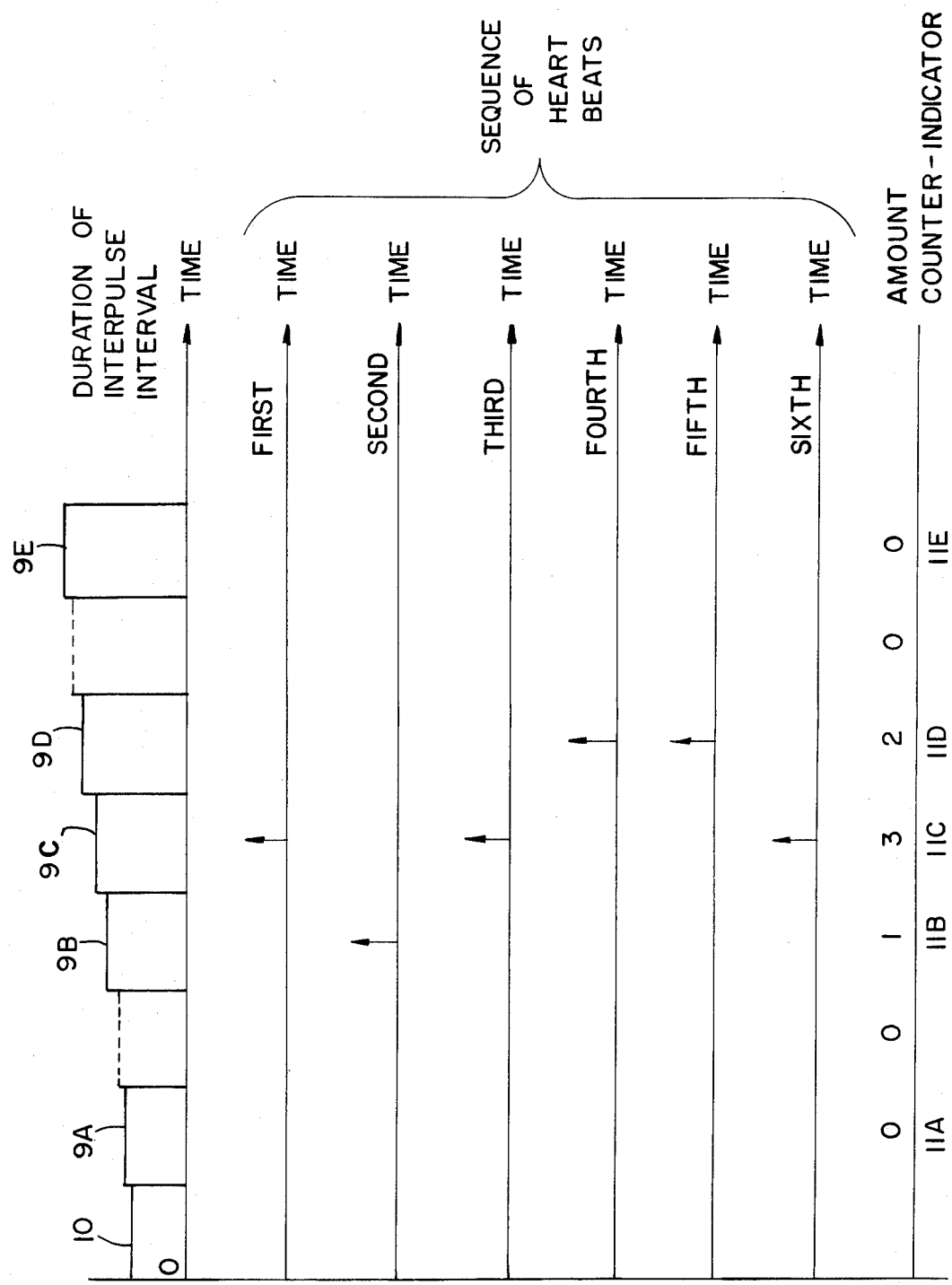
FIG. 4 is a set of graphs showing the intervals of time between successive heart beats, and the corresponding presentation of counts on indicators measuring the interpulse intervals.

Since each of the multivibrators 9 provides an output pulse of predesignated duration, the succession of multivibrator operations provides for a measurement of an interval of time between two heart beats. Thus, if the output signal of the multivibrator 9A is present, then the interpulse interval between two heart beats is relatively short, if the output pulse of the multivibrator 9C is present, then the interpulse interval is of nominal duration while, in the event that the output pulse of the multivibrator 9D is present, then the interpulse interval is of relatively long duration. Excessively long interpulse intervals result in the appearance of the output logic 1 signal of the flip-flop 9E which signal is retained until the appearance of the next pulse from the detector 1. The delay of the unit 10 establishes a minimal length or duration of the interpulse interval for the beginning of the first measurement period by the multivibrator 9A. The successive intervals of time as represented by the delay unit 10 and the succeeding ones of the multivibrators 9 are depicted in the first graph of FIG. 4. It is to be understood that the first graph of FIG. 4 is stylized and shows all of the measuring periods to be of equal length, it being understood that the delay of the unit 10 is substantially longer than the duration of the output pulses of the multivibrators 9A–9D, while the duration of the output signal of the flip-flop 9E is indefinite. It is also noted that the predesignated durations of these output pulses may be equal or unequal in accordance with the requirements of the histogram to be produced. Typically, the output pulses of the multivibrators 9 for the mid-range duration of interpulse intervals would be of equal duration.

Also shown in FIG. 1 are counters 11 and switches 12, individuals ones of the counters and of the switches being further identified by the legends A–E. Two sources of sound, such as exemplary buzzers 13A and 13B, are also provided. Each of the counters 11 is understood to include an indicator for displaying the count and well-known decoding and driving circuitry for converting the count to electrical signals for operation of the indicator. Typically, the indicators are alphanumeric indicators of the form commonly found in digital clocks and watches. The counter 11A counts the appearances of pulses, detected by the detector 1, which have occurred after an interpulse period within the measuring interval of the multivibrator 9A. The correspondence between the counts of the respective counters 11A-11E and the measuring intervals of the multivibrators 9A-9D and flip-flop 9E is depicted in the graphs of FIG. 4. The readings presented on the indicators of the counters 11A-11E are shown in the bottom graph of FIG. 4. The occurrences of exemplary pulses in a sequence of heart beats are presented in the sequence of graphs between the top and bottom graphs of FIG. 4.

For example, in reading the graphs of FIG. 4, it is assumed that a previous pulse has been detected by the detector 1 to start the measuring operation. The first pulse of the exemplary sequence is thus seen to occur after an interval of time, measured from the preceding pulse, which terminates during the measurement period of the multivibrator 9C. The second pulse of the sequence occurs during the measurement period of the multivibrator 9B, the subsequent pulses occurring during the measurement period of the multivibrators 9C and 9D. The counts by the counters 11A-11E are thus seen to register zero in the foregoing exemplary sequence, there being a count of 1 in the indicator of the counter 11B, a count of 3 with respect to counter 11C, and a count of 2 with respect to the counter 11D.

The buzzers 13A and 13B are connected individually by the switches 12A-12E, in a manner to be described subsequently, to the circuitry channel associated with each of the multivibrators 9A-9E and the counters 11A-11E so as to provide a buzzing sound, or other type of sound. The sound notifies the person wearing the monitor of the invention of the presence of interpulse intervals that are relatively short, and interpulse intervals that are relatively long. By use of the switches 12A-12E, the buzzing tone can be associated with any pair of the counters 11A-11E. In addition, the tone of the buzzer 13A may be made relatively high, this corresponding to a short interpulse interval and a high repetition frequency, while the buzzer 13B may provide a tone of relatively low pitch, this corresponding to the relatively long interpulse intervals and relatively low repetition frequency.

The circuit of FIG. 1 further comprises an AND gate 14, a clock 15, a counter 16, a pulse forming circuit or pulser 17, and a generator 18. The generator 18 is of the form known as a random-noise generator which provides trigger pulses at its output terminal, the interpulse intervals between the output trigger pulses having durations which vary in a random manner. In response to each of these trigger pulses, the pulser 17 provides pulses of uniform pulse width, the interpulse intervals varying in accordance with the variation of interpulse interval of the trigger pulses from the generator 18. The pulse width of the pulses provided by the pulser 17 are adjustable, but have a nominal pulse width of 10 milliseconds (ms). The output pulse from the pulser 17 is fed to one input terminal of the AND gate 2. At the other input terminal of the AND gate 2, there is fed the aforementioned output pulse of the detector 1, which pulse has a width of one millisecond.

The clock 15 has three output terminals coupled to switch section 7B for selectively providing sequences of clock pulses to one input terminal and the AND gate 14, the other input terminal of the gate 14 being coupled to the output terminal of the flip-flop 3. The clock pulses of the clock 15 are provided at rates of 1,000 pulses per second (pps), 100 pps and 10 pps, respectively, at the left, middle and right hand terminals of switch section 7B. These pulses are passed by the gate 14 to the counter 16 when the gate 14 is activated by the logic 1 signal at the output terminal of the flip-flop 3. As will be explained subsequently, the duration of the logic 1 signal of the flip-flop 3 is equal to the interpulse interval between two successive heart beats. Thus, the counter 16 counts clock pulses during the interpulse interval. The magnitude of the count of the counter 16 and its relationship to other parameters of the measurement process will be explained subsequently.

Also included in the circuit of FIG. 1 are a multivibrator 19, counters 20 with individual ones thereof being identified by the legends A-E, AND gates 21 with individual ones thereof being further identified by the legends A-E, and diodes 22. The counters 11, the gates 21, the multivibrators 9 and the delay unit 10 comprise a histogram unit 23 which is identified in the drawing as a dashed block.

The multivibrator 19 has two output terminals, labeled A and B, the signals thereof being complements of each other. The two output signals of the multivibrator 19 are useful in connecting the circuit of FIG. 1 to external apparatus, such as recording apparatus (not shown) which may be coupled to the counters 11 and 20 to provide a permanent readout of data of the counters on paper or other suitable medium. Upon attainment of the logic 1 signal at the selected output terminal of the counter 5, a logic 1 signal appears at terminal A of the multivibrator 19. The signal at terminal A is useful as a strobe for activating such recording equipment. After a sufficient interval of time has elapsed for the transference of data from the counters 11 and 20 to the external recording equipment, the multivibrator 19 returns to its original state whereupon the signal at terminal B assumes a logic 1 state. Thus, the signal at terminal B is useful as a reset signal, the terminal B being connected to all of the counters in the cuircuit of FIG. 1 for resetting these counters to zero. Thus, the counter 5, the counter 16 and the counters 1 and 20 are all reset to zero by the signal at terminal B so as to permit continuation of the measuring process whereby the measurement can be updated periodically.

The counters 20 represent successive stages of the counter 16, the complete series connection of the counter 16 through the counters 20A-20E providing a complete count of the clock pulses of the clock 15 through a measuring sequence until the resetting by the multivibrator 19. Each of the counters 20A-20E is understood to include an indicator, as well as a decoder and a driver for converting the count of the counter to electrical signals which place the count on the indicator.

A feature in the use of the counters 16 through 20E may be readily understood by considering the situation wherein the switch 7 is set to receive the logic 1 signal from the counter 5 after the counting of 100 heart beats. The total elapsed time of the sequence of heart beats, as measured by the counters 16 through 20E, is to be divided by 100 to give the elapsed time of the average interpulse interval. In the construction of the encoding and driving circuits of the counters 20A-20E, the division by 100 is automatically accomplished so that the indicators read the duration of the average interval directly. In the event that the switch 7 (section 7A) is set for the counting of 1,000 or 10,000 pulses, then the corresponding rate of clock pulses from the clock 15 is coupled by switch section 7B and gate 14 to provide indicated values of the counters 20A–20E wherein further factors of 10 or 100 have been introduced to compensate for the increased number of measurement intervals utilized in the computation of the average interval.

As a further convenience in the use of the counters 20A–20E, the individual indicators of the counters 20A–20E are located adjacent the indicators of the corresponding counters 11A–11E as shown in the arrangement of FIG. 2. Thereby, for the situation wherein the heart beats occur at a constant repetition frequency a numerical value appears in only one of the indicators of the counters 11 and, accordingly, the corresponding duration of the interpulse interval appears in the adjacent indicator of the counters 20.

The counting of the heart beats by the counters 11A–11E is accomplished by coupling the pulse signals of the detector 1 along line 24 through corresponding ones of the AND gates 21A–E. Each of the gates 21A–D is activated by the output signal of the corresponding one of the multivibrators 9A–9D, and the gate 21E is activated by the output logic 1 signal of the flip-flop 9E. Thus, while the output pulse signal of the detector 1 is coupled by line 24 simultaneously to each of the AND gates 21, only that one of the gates 21 which is activated by a multivibrator 9 or flip-flip 9E passes the pulse signal from the detector 1 to the requisite one of the counters 11. In this way, there is a correspondence between the number of pulses having the same duration interpulse interval, this being provided by the counters 11, and the duration of an average interpulse interval, this being provided by the counters 20. The output terminals of the AND gates 21A–E are also coupled by the diodes 22 to the respective ones of the switches 12A–E for activating the buzzers 13A–B as was described previously.

By way of example, in the foregoing relationship between the counts of the counters 11 and the counts of the counters 20, it is assumed that the person has a pulse rate of 80 beats per minute. The switch 7 is set to apply the output signal of the counter 5 to the gate 6 at the conclusion of 100 counts by the counter 5. At the pulse rate of 80 beats per second, a total time of 75 seconds is elapsed during the counting of the pulses of the clock 15 by the counters 16 and 20. Since the indicators of the counters 20 have been set with the decimal point moved two places to the left so as to automatically provide for the division by 100, an indicator of the counters 20 reads an average interpulse interval of 0.75 seconds. For the purposes of this example, it is further assumed that the pulse rate is constant so that the counting of beats on the line 24 is accomplished completely by only one of the counters 11. Again, for purposes of example, the total delay produced by the delay unit 10 plus that of the multivibrators 9A through 9C is assumed to be equal to approximately 0.75 seconds. Accordingly, the indicator of the counter 11C reads the value of 100 pulses, and the indicator of the counter 20C reads the value of 0.75 seconds for the interpulse interval.

Continuing with a further example, a constant pulse rate of 120 beats per second and a corresponding interpulse interval of 0.50 seconds is assumed. The total of 100 counted pulses appears on the indicator of the counter 11A and the average interpulse interval of 0.50 seconds appears on the indicator of the counter 20A. As yet a further example, it is assumed that there is a constant pulse rate of 60 beats per second and a corresponding interpulse interval of 1.0 seconds. A total count of 100 pulses then appears on the indicator of the counter 11E while the average interpulse interval of 1.0 seconds appears on the indicator of the counter 20E.

With reference to FIGS. 2 and 3, there is shown a heart monitor 25 embodying the circuitry of FIG. 1 and having a display 26 for the presentation of the data of the counters 11 and 20. The monitor 25 is secured by a band 27 to the wrist 28 of the person whose heart beat is being monitored. With respect to the foregoing presentation of data of the interpulse intervals and of the number of heart beats, it is noted that the data is presented in the indicators of the counters 20 and 11 corresponding to the specific ranges of values. Thus, the high pulse rates and short interpulse intervals are described by data appearing in the counters 20A and 11A. Very slow pulse rates and very long interpulse intervals are presented in the counters 20E and 11E. The midrange of values of pulse rate and interpulse interval are described by data in the counters 20C and 11C. Thereby, the location on the display 26 is determinative of the range of values, while the specific numerals appearing in the indicators give more precise information. Thus, with respect to the foregoing examples, the range of short values of interpulse intervals presented by the counters 11A and 20A are in the range of 0.46–0.55 seconds corresponding approximately to a high pulse rate of 110–130 beats per second. With respect to the long interpulse intervals of the counters 11E and 20E, the exemplary range of values is in excess of 0.97 seconds corresponding to a pulse rate less than approximately 62 beats per second.

Other ranges are as follows. At the middle value, the counters 11C and 20C present data as to interpulse intervals of duration 0.73–0.77 corresponding to a range of pulse rates of approximately 78–82 pulses per second. To complete the foregoing example with contiguous values of range provided by the counters 11B and 20B and the counters 11D and 20D, the following exemplary values may be utilized. For the counters 11B and 20B, the range of interpulse intervals is 0.69–0.72 seconds corresponding to approximately a pulse rate of 83–88 pulses per second. For the counters 11D and 20D, the interpulse interval may be 0.78–0.82 seconds corresponding to a pulse rate of approximately 73–77 pulses per second.

The foregoing examples were for cases of constant pulse rate. However, a most important case is the situation wherein the pulse rate varies. For example, let it be assumed that during a counting of 100 heart beats, 50 beats occur with interpulse intervals of 0.75 seconds, 25 heart beats occur with interpulse interintervals of 0.50 seconds, and another 25 heart beats occur with interpulse intervals of 1.00 seconds. The total amount of elapsed time, as measured by the counters 16 and 20, is 75 seconds. Thus, the average interpulse interval is 0.75 seconds, which value appears on the indicator of the counter 20C. The count of the 50 pulses having the interpulse interval of 0.75 seconds is presented by the counter 11C. The count of the 25 pulses having the interpulse interval of 0.50 seconds is presented by the counter 11A. The count of 25 pulses having the interpulse interval of 1.00 seconds is presented by the counter 11E.

Thereby, an important feature of the invention appears in the mode of presentation of data on the display 26. In the foregoing example of a non-uniform pulse rate, arrhythmia, three indicators associated with the counters 11A, 11C and 11E are illuminated on the display 26 of FIG. 2. These indicators present the number of beats occurring in three different ranges of interpulse intervals. Only one of the indicators associated with the counters 20, namely the counter 20C, is illuminated to present the average interpulse interval of all of the 100 heart beats. Since the indicator of the counter 20C appears in the middle of the arrangement of the illuminated indicators associated with the counters 11, the display 26 informs a viewer that the distribution of interpulse intervals is symmetric. In the event that most of the heart beats were at the lower rate corresponding to the longer interpulse intervals, then the indicator associated with the counter 20D would be illuminated showing a skewed distribution of the interpulse intervals. Similarly, in the event that most of the beats occurred at the higher frequency corresponding to the shorter interpulse intervals, then the indicator of the counter 20B would be illuminated showing a skewed distribution of interpulse intervals. Thereby, the patient or the physician can immediately determine whether the arrhythmia is characterized by a symmetric or an assymmetric distribution of the heart beats and interpulse interval.

In operation, therefore, the monitor 25 is attached to the wrist 28 with the detector 1 positioned for receiving the pulses resulting from each of the heart beats. With each occurrence of an interpulse interval that is to be measured, a pulse from the delay unit 8 resets all of the multivibrators 9 and the flip-flop 9E and then, via the delay unit 10, initiates a chain reaction among the multivibrators 9 in which each multivibrator provides an output pulse to its corresponding AND gate 21 for a predesignated amount of time, after which the multivibrator triggers the next multivibrator to provide its output pulse for a predesignated amount of time to its corresponding AND gate 21. Depending on the duration of the interpulse interval, the next pulse arriving on line 24 is passed to the appropriate section of the counters 11 by the corresponding one of the AND gates 21 which is being activated by its multivibrator 9. Thereby the multivibrators 9 set up a sequence of time slots corresponding to various interpulse intervals during which heart beats are to be counted by the counters 11. Also, upon the appearance of the pulse at the output terminal of the delay unit 8, the flip-flop 3 is activated to operate the AND gate 14 to pass clock pulses from the clock 15 to the counters 16 and 20. The elapsed time counted by the counter 16 corresponds, assuming the presence of an average pulse rate, to the length of time in the delay of the delay unit 10. Thereby, no count appears on an indicator of the counters 20 except for counts corresponding to ranges of interpulse intervals falling within the time slots set by the multivibrators 9 and the flip-flop 9E subsequent to the delay initiated by the delay unit 10. With respect to the foregoing exemplary values of interpulse ranges, the range for the counter 11A was given as 0.46-0.55 seconds, this being the minimum length of interpulse intervals to be measured by the monitor 25. Accordingly, the delay unit 10 of FIG. 1 would provide a delay of 0.45 seconds. The delay of the delay unit 8 is much shorter than the durations of signals appearing in the circuitry of FIG. 1, so as not to alter the time measurements by the circuitry. Accordingly, the delay of the delay unit 8 is on the order of 10-100 microseconds.

The foregoing operation of the circuitry of FIG. 1 is accomplished in either one of two modes. The operation may follow a direct mode wherein every interpulse interval is measured, or may follow a statistical mode in which the interpulse intervals are selected statistically for being measured. In the direct mode, the switch 4 couples the output pulse signals of the detector 1 directly to the counter 5. In the statistical mode, the output pulses of the detector are coupled via the AND gate 2 through the switch 4 to the counter 5. The operation in the two cases is best understood with reference to FIGS. 5 and 6.

Figure 5:
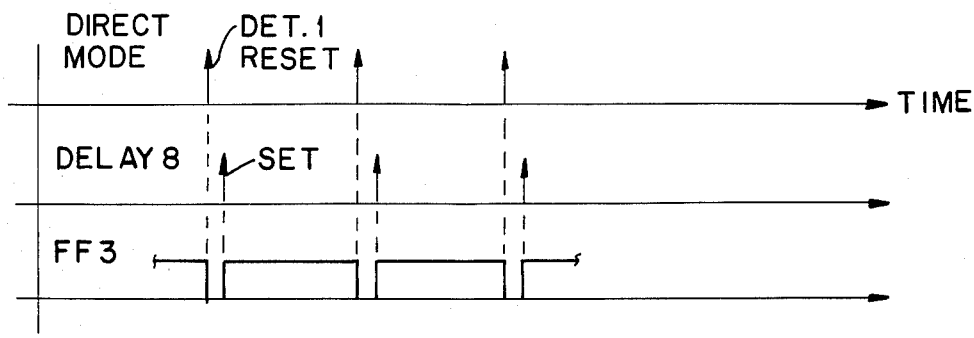
FIG. 5 is a set of graphs of a timing diagram showing the relationships between the setting and resetting of a flip-flop of FIG. 1 relative to the occurrences of a heart beat, the successive settings of the flip-flop being used for determining measuring intervals.

FIG. 5 contains three graphs in time registration for demonstrating the operation of the direct mode in which the output pulses of the detector 1 are coupled via the switch 4 directly to the counter 5 and to the AND gate 6. In both modes of operation, the output pulses of the detector 1 are applied via line 24 directly to the reset terminal of the flip-flop 3 and to an input terminal of each of the AND gates 21. A succession of the pulses on line 24 is depicted in the first graph of FIG. 5. During the counting by the counter 5, the output terminal thereof, coupled to the switch 7, provides a logic 0 signal to the complemented input terminal of the gate 6 so as to enable passage of the pulses from the detector 1 via the gate 6 into the delay unit 8. After a relatively short delay in the delay unit 8, on the order of 10-100 microseconds, the delay unit 8 applies the pulse to the set terminal of the flip-flop 3, and also to the reset terminals of each of the multivibrators 9 and the flip-flop 9E. A sequence of output pulses of the delay unit 8 is depicted in the second graph of FIG. 5, the second graph showing a succession of settings of the flip-flop 3 which are seen to occur shortly after the resetting accomplished by the pulses of the first graph of FIG. 5. In the third graph of FIG. 5, the operation of the flip-flop 3 is depicted, the graph showing the output signal of the flip-flop 3 attaining a logic 1 at the occurrence of a set pulse of the second graph, the output signal of the flip-flop 3 returning to the value of logic 0 upon the occurrence of a reset pulse of the first graph of FIG. 5. Since the output signal of the flip-flop 3 controls the operation of the AND gate 14, clock pulses from the clock 15 are applied via the gate 14 to the counters 16 and 20 only during such time as the output signal on the flip-flop 3 is at a logic 1 as depicted in the third graph of FIG. 5. Since the delay introduced by the delay unit 8 is much smaller than the spacings and duration of other pulses generated in the circuitry of FIG. 1, the delays appearing between successive output signals of the flip-flop 3 introduce no error into the measurement of the average interpulse interval nor into the counting of the number of pulses occuring in any one of the time slots provided by the multivibrators 9.

Figure 6:
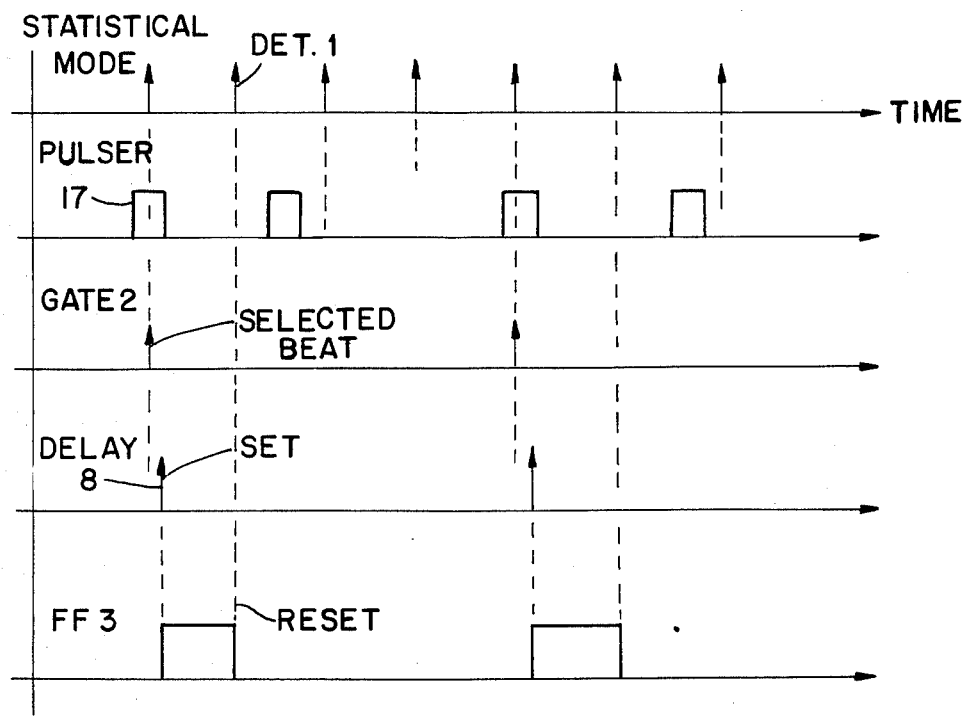
FIG. 6 is a set of graphs comprising a timing diagram similar to that of FIG. 5, for the implementation of a statistical sampling and measuring of heart-beat data.

FIG. 6 shows the operation of the circuitry of FIG. 1 for the statistical mode. FIG. 6 includes five graphs, the first graph of FIG. 6 being the same as the first graph of FIG. 5. The third graph of FIG. 6 is similar to the first graph of FIG. 1 but differs therefrom in that a number of pulses have been deleted. The fourth graph of FIG. 6 is similar to the second graph of FIG. 5, but differs therefrom in that a number of pulses have been deleted. The fifth graph of FIG. 6 is similar to the third graph of FIG. 5, but differs therefrom in that a number of the output pulse signals of the flip-flop 3 have been deleted. By the deletion of the foregoing pulses, the operation of measuring interpulse intervals over a set of 100 heart beats is thus extended over a much longer interval of time. For example, if, on the average, only one interpulse interval were measured per minute, then the entire measurement procedure would take 100 minutes. By the deletion of still more pulses so that, on the average, only 10 interpulse intervals are measured per hour, then the measurement process would extend over a period of 10 hours.

For the statistical mode, the detection and selection of heart beats is accomplished as follows. Since the trigger signals produced by the generator 18 occur only at random intervals, the output pulses of the pulser 17, having typically a ten millisecond duration, occur at random intervals. The output pulses of the pulser 17 are depicted in the second graph of FIG. 6. The output pulses of the detector 1, appearing on line 24 and also in the first graph of FIG. 6, have a duration much smaller than the output pulses of the pulser 17, typically the aforementioned 1 ms. The coupling of the output pulses of the detector 1 and of the pulser 17 and to the AND gate 2 is depicted in the second graph of FIG. 6. Therein, it is seen that while the heart beats occur at a substantially regular rate, the pulses from the pulser 17 may occur infrequently and, accordingly, overlap the occurrences of the pulses of the detector 1 at infrequent occurrences. Such overlapping is depicted in the second graph of FIG. 6. Only during the coincidence of occurrences of the output pulses of the detector and the pulses 17 does an output pulse appear from the gate 2. Such selected output pulse, corresponding to a selected heart beat, appears in the third graph of FIG. 6. The corresponding set signal at the output terminal of the delay unit 8 appears in the fourth graph of FIG. 6 for setting the flip-flop 3, the resetting thereof occurring upon the next output pulse of the detector 1 as depicted in the first and fifth graphs of FIG. 6. It is noted that, since the output pulses of the detector 1 are fed directly to the reset terminal of the flip-flop 3, the flip-flop is always preset with the next occurrence of a heart beat, independently of the position of the switch 4. Thus, as depicted in the fifth graph of FIG. 6, there are a succession of widely spaced output pulses of the flip-flop 3, each of which pulses has a duration equal to an interpulse interval between two successive heart beats. Accordingly, the counters 11 and 20 operate in the same fashion, both in the direct mode and in the statistical mode, with counting being done during the presence of logic 1 signals at the output terminal of the flip-flop 3. In t'\ direct mode, the output logic 1 signals of the flip-flop 3 occur immediately, one after the other. In the case of the statistical mode, these output logic 1 signals of the flip-flop 3 are widely spaced in time. By adjusting the duration of the pulse width of the output pulses of the pulser 17, the chances of a coincidence occurring between pulses of the detector 1 and of the pulser 17, first and second graphs of FIG. 6, are reduced so that a longer measurement period results.

Yet another feature of the invention is obtained by incorporating a watch circuit 29 within a housing 30 of the monitor 25. The watch circuit 29 is of conventional design, the circuit 29 being of a form utilized in conventional digital watches and including a conventional indicator of time which is centered in the display 26. The clock 15 which drives the circuitry of FIG. 1 also drives the watch circuit 29. Thereby, the monitor 25 can be worn and utilized as a conventional wrist watch while further serving the function of providing heart-beat data.

By way of alternative embodiments of the invention, it is noted that the foregoing circuitry can also be contained within larger equipment such as within a housing (not shown) suitable for carrying within a physician's pocket, or within a desk model (not shown) to be set on a physician's desk. The pocket sized model is advantageous in that it can be more easily read since the display is larger than the foregoing embodiment which is worn on the wrist. The desk model is advantageous in that the digitized data of the counters can be readily applied by wellknown circuitry to a microcomputer contained within the desk model. The microcomputer would provide a graphical display of the histogram corresponding to the numerical display of the wrist model. Such display would be presented on a screen such as that used in "home computers". In both the pocket and desk models, the detector of the heart-beat pulse would be mounted on an adjustable bracelet and be connected by a flexible electrical cord to the other components of the electrical circuit which would be contained within the housing of the pocket model or the desk model. The adjustable bracelet permits the physician to place the detector on the patient's wrist during an examination in the physician's office.

It is to be understood that the above described embodiment of the invention is illustrative only and that modifications thereof may occur to those skilled in the art. Accordingly, this invention is not to be regarded as limited to the embodiment disclosed herein, but is to be limited only as defined by the appended claims.

What is claimed is:

1. A heart monitor comprising:
   a housing adapted to be worn on a person;
   a display of heart-beat data supported by said housing, said display including indicators of duration of interpulse intervals between successive beats of the heart, and counts of heart beats occurring within predetermined ranges of interpulse intervals;
   the indicators of duration of interpulse intervals being located at sites corresponding to sites of the locations of the indicators of the counts of the heart beats to show symmetric and skewed distribution of interpulse intervals; and
   electronic circuitry enclosed within said housing and responsive to heart beats of said person for driving said indicators, said circuitry including a detector of heart beats, means coupled to said detector for counting heart beats, means coupled to said counting means for designating a sequence of measurement intervals, and means coupled to said designating means for measuring the duration of interpulse intervals and the number of beats occurring in each of said ranges, said measuring means being coupled to said indicators.

2. A monitor according to claim 1 wherein said detector produces an output signal comprising a sequence of pulses, each of said pulses corresponding to detection of a heart beat, and wherein said designating means includes means for designating one of said pulses at a beginning and another of said pulses at an end of each of said measurement intervals.

3. A monitor according to claim 2 wherein said measuring means comprises a clock which generates a sequence of clock pulses, a counter which counts clock pulses, a gate coupling said counter to said clock, and wherein said gate is operatively connected to said designating means for applying clock pulses to said counter.

4. A monitor according to claim 2 wherein said measuring means comprises a set of gates, a set of sequentially activated circuits which operate said gates, and a set of counters, said gates coupling pulses from said detector to individual ones of said counters for counting the number of beats occurring in each of said ranges of interpulse intervals.

5. A monitor according to claim 2 wherein said designating means comprises flip-flop means for signalling the beginning and end of an interpulse interval, and delay means coupled between said detector and an input terminal of said flip-flop means for delaying the application of a pulse of said detector to said flip-flop means, another input terminal of said flip-flop means being coupled directly to said detector.

6. A monitor according to claim 5 wherein said designating means further comprises means for generating a random series of gating pulses, and gating means coupled between said generating means and said detector for gating pulses of said detector to said counting means.

7. A monitor according to claim 6 wherein said designating means further comprises a switch coupled between said gating means, said detector, and said counting means for switchably connecting an input terminal of said counting means to said detector and said gating means.

8. A monitor according to claim 7 wherein said measuring means comprises a set of gates, a set of sequentially activated circuits which operate said gates, a set of counters coupled respectively to individual ones of said gates, and wherein an input terminal of each of said gates is coupled to said detector for applying pulses of said detector to respective ones of said counters.

9. A monitor according to claim 8 wherein said measuring means further comprises a clock, a counter of pulses produced by said clock, and a gate connecting pulses of said clock to said counter, said gate being operated by a signal of said designating means.

10. An analyzer of pulsation comprising:
means for detecting pulses of a sequence of said pulses, said pulses being separated by interpulse intervals;
means coupled to said detecting means for measuring an average value of said interpulse intervals;
means coupled to said detecting means for measuring the frequency of occurrence of individual ones of said interpulse intervals; and
means coupled to said average-value measuring means and to said occurrence measuring means for presenting data of said average value in visual correspondence with data of said frequency of occurrence.

11. An analyzer according to claim 10 further comprising means coupled to said detecting means for designating pulses at the beginning of interpulse intervals and pulses at the end of interpulse intervals, said designating means applying the designated pulses to said means for measuring the average value.

12. An analyzer according to claim 11 wherein said means for measuring the average value comprises a clock, a counter, and a gate operated by a gate signal of said designating means, said gate coupling pulses of said clock to said counter, said counter counting said pulses of said clock during an interval established by said designating means.

13. An analyzer according to claim 11 wherein said means for measuring the frequency of occurrence comprises a set of gates and a set of sequentially activated circuits for operating said gates, said circuits being activated by a strobe signal from said designating means, said means for measuring the frequency of occurrence further comprising a set of counters coupled via said gates to said detecting means for counting pulses occurring during interpulse intervals of predesignated durations.

14. An analyzer according to claim 11 wherein said designating means further comprises flip-flop means having an input terminal coupled directly to said detecting means, and delay means coupled between said detecting means and a second input terminal of said flip-flop means for delaying the signal of said detecting means to said flip-flop means, said flip-flop means providing a gate signal to said means for measuring the average value.

15. An analyzer according to claim 14 wherein said designating means further comprises means for generating a random series of gating pulses and coincidence means responsive to the coincidence of output signals of said detecting means and said gating pulses for coupling signals of said detecting means to said delay means to provide a statistical distribution of interpulse intervals.

16. An analyzer according to claim 15 further comprising switch means coupled between said coincidence means, said detecting means and said delay means for switchably coupling said detecting means and said coincidence means to said delaying means, thereby selecting a statistical mode or direct mode of measurement.

17. An analyzer according to claim 16 further comprising means coupled between said switch means and each of said measuring means for establishing a length of said sequence of pulses.

18. An analyzer according to claim 17 wherein said means for measuring the average value comprises a clock, a counter, and gating means activated by a signal of said designating means for applying pulses of said clock to said counter, and wherein said means for measuring the frequency of occurrence comprises a set of counters, a set of gates coupling signals of said detecting means to respective ones of the counters of said set of counters, and a set of sequentially activated gating circuits responsive to signals of said delay means for operating the gates of said set of gates.

* * * * *